United States Patent [19]

Luther

[11] Patent Number: 4,650,466
[45] Date of Patent: Mar. 17, 1987

[54] ANGIOPLASTY DEVICE

[75] Inventor: Ronald B. Luther, Newport Beach, Calif.

[73] Assignee: Angiobrade Partners, Santa Ana, Calif.

[21] Appl. No.: 793,793

[22] Filed: Nov. 1, 1985

[51] Int. Cl.$^4$ .............................................. A61M 37/00
[52] U.S. Cl. ..................................... 604/95; 604/105; 604/266; 128/343; 128/348.1
[58] Field of Search ............ 604/95, 96, 105, 107–109, 604/206; 128/341–343, 345, 1 R, 325, 334, 348.1

[56] References Cited

U.S. PATENT DOCUMENTS

| | | | |
|---|---|---|---|
| 2,498,692 | 2/1950 | Mains | 604/95 |
| 2,816,552 | 12/1957 | Hoffman | 128/341 |
| 3,416,531 | 12/1968 | Edwards | 604/95 |
| 3,433,226 | 3/1969 | Boyd | 604/22 |
| 3,568,659 | 3/1971 | Karnegis | 604/105 |
| 3,605,725 | 9/1971 | Bentov | 604/95 |
| 3,623,483 | 11/1971 | Dyer | 604/266 |
| 3,773,034 | 11/1973 | Burns et al. | 604/95 |
| 3,868,956 | 3/1975 | Alfidi et al. | 128/345 |
| 3,996,938 | 12/1976 | Clark, III | 128/348.1 |
| 4,572,186 | 2/1986 | Gould et al. | 128/343 |
| 4,577,631 | 3/1986 | Kreamer | 128/325 |
| 4,607,618 | 8/1986 | Angelchik | 128/345 |

FOREIGN PATENT DOCUMENTS 0867144 2/1953 Fed. Rep. of Germany ........ 604/96
8303752 11/1983 World Int. Prop. O. .......... 128/1 R Primary Examiner—C. Fred Rosenbaum
Assistant Examiner—Mark Rooney
Attorney, Agent, or Firm—Willie Krawitz

[57] ABSTRACT

An angioplasty device is disclosed comprising a woven tube of metal or plastic fibers and a retraction stylet that are attached at one end to a catheter tube for insertion into a vein, artery and the like for the removal of plaque and similar material. One or more guide wires or a stylet may be attached to the woven tube for rotation and manipulation inside the artery. When the stylet or guide wires are retracted, the woven tube expands and contacts the interior, plaque-coated wall of the artery. Movement of the guide wires and expanded woven tube will abrade atherosclerotic plaque from the artery to form particles which are trapped within the tube. An expandable fabric within the woven tube which opens and closes with the corresponding expansion and closure of the woven tube may be used to collect the trapped particles. Removal of the angioplasty device from the artery will them remove the atherosclerotic particles from the patient.

12 Claims, 6 Drawing Figures

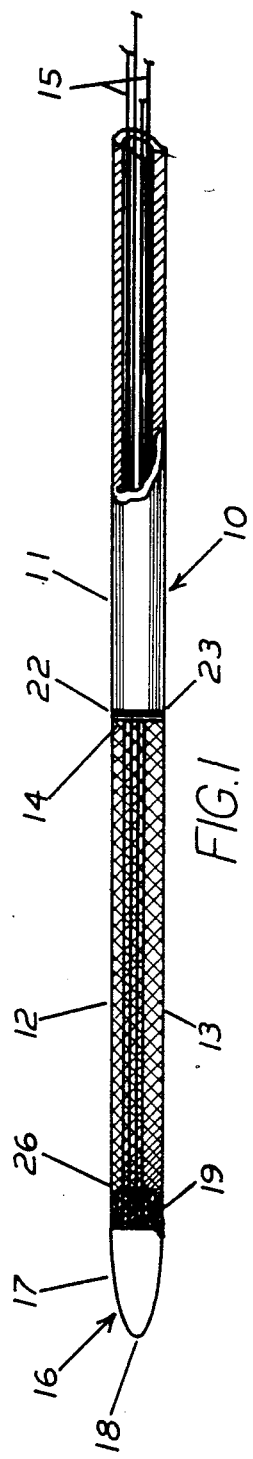
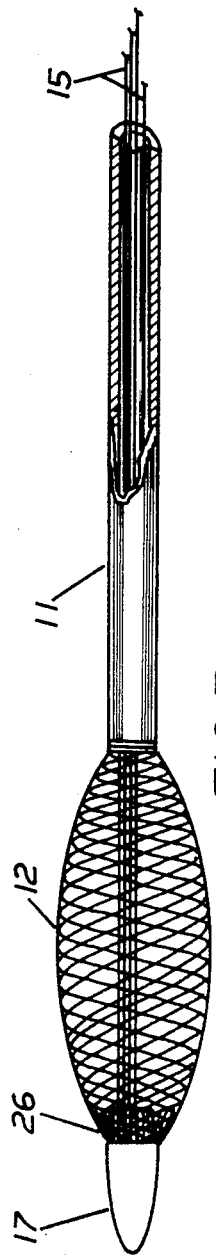
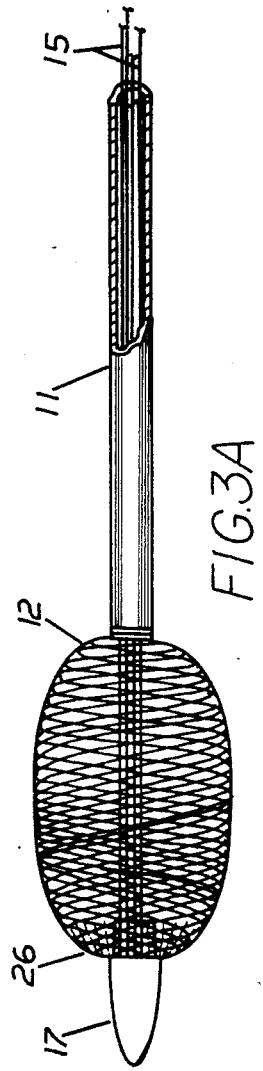

ANGIOPLASTY DEVICE

BACKGROUND OF THE INVENTION

This invention relates to a new and improved angioplasty device for removing and/or compressing atherosclerotic plaque, for thromboses, stenoses, occlusions, clots, potential embolic material, and so forth from veins arteries, and the like. The device also has potential for treatment of the following conditions which appear in recent literature as candidates for angioplasty therapy: artifical stenoses, percutaneous aspiration thromboembolectomy, venostenotic lesions, cerebral embolization, renal artery stenosis, coronary artery diseases, vena cavity bleeding, congenital pulmonary valve stenosis, lower extremity vein graft stenosis, streptokinase thrombus infusion, lower extremity atherosclerotic lesions, incomplete obstruction of the vena cava, intracranial fistulas, cardiac pacing, diagnostic catheterization, renal infarction with uncontrollable hypertension, stenotic coronary lesions, intrahepatic strictures, pulmonary artery stenosis, coarctation of the aorta, gastrointestinal stenosis, peripheral pulmonary stenosis, esophageal strictures, carotid artery stenosis, chronic total coronary artery occlusion, nonorganized atheroma, dialysis access fistula stenosis, baffle obstruction of vena cava, ruptured cerebral aneurism, vertebral artery traumatic fistula, distal multivessel coronary artery disease, hypoplastic right heart syndrome, ureter strictures, carotid cavernous fistula, fibromuscular dysplasia of carotid artery, limb salvage, ureteral strictures in graft kidneys, atherosclerosis of abdominal aortic bifurcation, ileofemoral atherosclerosis, and acute myocardial infarction.

Prior art devices include catheters fitted with an inflatable balloon that either displaces an obstruction from a vessel or compresses material such atherosclerotic plaque and the like against a vessel wall.

Various problems have been associated with the use of balloon tipped catheters, such as vessel dissection, perforation, rupture, conversion of a stenosis to an occlusion, thromboembolism atheroembolism, gas embolism, balloon rupture and embolization, and arteriotomy have all been reported. Coronary angioplasty has produced complications such as coronary dissection, acute myocardial infarction, emergency bypass surgery, and death.

In addition to the foregoing problems, angioplasty devices employing balloons do not remove atherosclerotic plaque, but simply compress the plaque against the sidewall of the vessel. Frequently however, the treated arteries revert to their approximate untreated condition. Moreover, during the treatment, arteries may become blocked, thereby causing a heart attack. Consequently, a surgical team must be on hand to treat the patient if this condition occurs.

It would be preferable to provide an angioplasty device that does not present problems such as caused by a balloon rupture, and which reduces the possibility of a blocked artery during use. Also, it would be desireable to physically remove some atherosclerotic plaque, and the like, in addition to compressing the plaque against the arterial side wall.

THE INVENTION

According to the invention, an angioplasty device and method of use therefor, is provided, comprising a woven tube of metal or plastic fibers moveable by means of guide wires, a stylet, etc., along an inner catheter tube, which are inserted into an artery, vein, and the like, for purposes of removing atherosclerotic plaque, and so forth, therefrom. The fibers are of sufficient size and resiliency so that when the woven tube is retracted by the guide wires or stylet, it will expand and contact the interior wall of the artery. Release of the retraction wires or stylet allows the woven tube to assume its original shape. The guide wires may be employed for inserting, positioning, retracting and rotating the woven tube within the vein or artery. Selective movement of the guide wires causes the fibers of the woven tube to remove particles of plaque, and the like from the artery wall where they are then collected by the woven tube. If desired, a filter trap may be positioned inside the woven tube to improve the particle collecting capability of the device. Consequently, when the device is removed from the patient, some of the atherosclerotic particles are also removed.

When the device is positioned in an artery, blood will flow through the expanded portion of the woven tube of fibers, and this reduces considerably the possibility of the artery from becoming totally blocked.

BRIEF DESCRIPTION OF THE DRAWINGS

FIG. 1 is a cross sectional view in side elevation showing the angioplasty device, according to the invention;

FIGS. 3 and 3A are cross sectional views in side elevation showing the device in two different stages of expansion; and, FIG. 4 is a cross sectional view in side elevation, showing a sonic vibrator mounted at one end of the device.

DESCRIPTION OF THE PREFERRED EMBODIMENTS

Figure 1A:
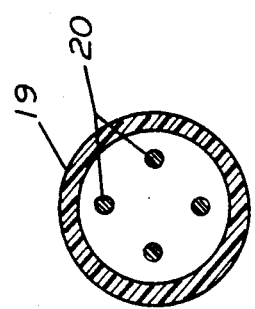
FIG. 1A is a view taken along lines 1A—1A of FIG. 1.

The angioplasty device 10 of this invention is shown in FIGS. 1 and 1A, and comprises an inner, hollow catheter tube 11 of a flexible plastic or spiral wire (which may be plastic coated) and is preceded by a woven tube 12 of fibers 13, that are bonded 14 to the catheter tube. The fibers 13 may be of plastic, stainless steel, etc., or a combination thereof, and their size and flexibility are selected so that when the woven tube 12 is compressed by an attached stylet or guide wires 15 against the bond 14, it will expand outwardly; this is shown in FIGS. 3 and 3A. When the guide wires are released, the woven tube 12 will revert to its original nonexpanded form, as shown in FIG. 1. Typically, the tube 12 is constructed as a braided weave.

Figure 2:
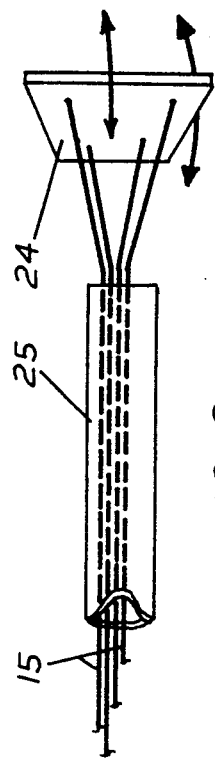
FIG. 2 is a cross sectional view, partially in perspective, showing a portion of the device, and means for manipulating and directing the device.

Bonded to the proximal end 16 of the catheter tube 11 is a steering head 17, having a rounded front portion 18 and a flat rear plate portion 19 which is perforated 20 for the insertion of the guide wires 15 therethrough. A plate 22 having perforations 23, and similar to the plate portion 19 is bonded to the catheter tube at or near the bond 14. The guide wires 15 pass through both sets of perforations 20, 23 in the respective plates 19 and 22, and the two plates function to align the guide wires and prevent them from becoming entangled. As shown in FIG. 2, the guide wires are attached to a steering plate 24 at the distal end 25 of the device 10, and this enables the device to be manipulated in the patient's artery or vein. If desired, the leading portion of the woven tube 12 may be lined by a filter cloth 26 of say nylon, polyester, etc., which expands with the woven tube and collects particles and debris removed from the artery. These particles are then removed when the angioplasty device is retracted from the patient.

When the angioplasty device 10 is inserted into an artery, its location can be determined by radiographic means and viewed by well known techniques. The device is positioned adjacent a plaque lined area within the artery, and the guide wires or stylet are retracted, thereby causing the woven tube 12 to expand, various degrees of expansion being shown in FIGS. 3 and 3A. With the woven tube in the expanded state, the device is manipulated such as by rotation, by moving backward and forward, and by vibration, etc. This will remove by abrasion, plaque and other material lining the inside of the artery wall. The extent of expansion is determined by the amount of constriction of the artery. Substances such as streptokinase may be injected to the abrasion site to assist in dissolving fibrin; urokinase and plaque dissolving material also may be used.

Figure 4:
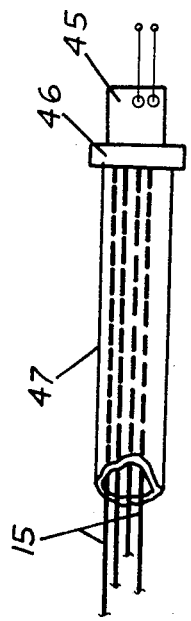

As illustrated in FIG. 4, a vibrator 45 is shown mounted to a steering plate 46, and the vibrator transmits oscillations through guide wires 15 to the abrasion site through the catheter 47 to assist in the removal of plaque from the artery.

The angiplasty device of this invention removes material lining the artery, and this reduces the possibility of the artery reverting to its original constricted state. Also, use of a woven tube during the angioplasty procedure reduces the possibility of the artery from becoming completely blocked. In addition, problems arising from using an expansion balloon, such as overinflation, thereby causing the artery to rupture, etc., will be obviated.

I claim:

1. An angioplasty device for insertion into a vein, artery, and the like for the treatment thereof, and compression and removal of foreign material, comprising:
   a. a hollow catheter for insertion into the vein or artery;
   b. a woven tubular fabric mounted forwardly of the catheter, and adapted for manipulation within the vein or artery the fabric being attached to the distal end of the catheter and extending distally therefrom to a tip member;
   c. guide wire means leading through the catheter and tubular fabric and attached to the distal end of the tubular fabric, the guide wires being adapted for retraction and release;
   d. aligning means positioned within the device for aligning the guide wires;
   e. steering means for the guide wires; and,
   f. a filter bag lining the distal end of the woven tube; whereby,
      i. the tubular fabric is adapted for expansion or contraction depending on the extent of retraction or release, respectively, of the guide wires;
      ii. in the expanded form, the device is adapted to be manipulated adjacent a treatment site in the vein or artery for treatment thereof, and for compression and removal of foreign material, the tubular fabric when expanded, being adapted to receive foreign particles that have been removed from the vein or artery, and to trap the particles when the fabric is contracted upon release of the guide wires;
      iii. the filter bag is adapted to expand or contract with a corresponding movement of the woven tubular fabric and to trap particles removed from the vein, artery, and the like; and,
      iv. when the device is removed from the vein or artery, the trapped particles in the filter bag are removed from the treatment site.

2. The device of claim 1, in which the catheter is a flexible plastic.

3. The device of claim 1, in which the catheter is a spiral wire.

4. The device of claim 3, in which the spiral wire is coated with a plastic.

5. The device of claim 4, in which the filter bag is comprised of a woven plastic fabric selected from the class consisting of nylon and polyester.

6. The device of claim 1, in which the tubular fabric comprises fibers selected from the class of plastic and stainless steel.

7. The device of claim 1, in which the tubular fabric is formed as a braided weave.

8. The device of claim 1, in which vibrating means are associated with the device to aid in the removal of foreign material from the vein or artery.

9. The device of claim 1, in which the alignment means comprise at least one perforated plate.

10. A method for treatment of an artery, vein and the like, and for compression and removal of foreign material therefrom with an angioplasty device, comprising:
   a. inserting a hollow catheter into the vein or artery;
   b. manipulating the device adjacent a treatment site;
   c. treatment thereof, compression and removal of foreign material from the vein or artery; and,
   d. trapping particles of the removed foreign material with the device and withdrawal of the device from the vein or artery, the device including:
      i. a hollow catheter for insertion into the vein or artery;
      ii. a woven tubular fabric mounted forwardly of the catheter, and adapted for manipulation within the vein or artery;
      iii. guide wire means leading through the catheter and tubular fabric and attached to the distal end of the tubular fabric, the guide wires being adapted for retraction and release;
      iv. aligning means positioned within the device for aligning the guide wires;
      v. a filter bag lining the distal end of the woven tube; and,
      vi. steering means for the guide wires; whereby:
         A. the tubular fabric is adapted for expansion or contraction depending on the extent of retraction or release, respectively, of the guide wires;
         B. in the expanded form, the device is adapted to be manipulated adjacent a treatment site in the vein or artery for treatment thereof, and for compression and removal of foreign material, the tubular fabric when expanded, being adapted to receive foreign particles that have been removed from the vein or artery, and to trap the particles when the fabric is contracted upon release of the guide wires;
         C. the filter bag is adapted to expand or contract with a corresponding movement of the woven tubular fabric and to trap particles removed from the vein, artery, and the like; and, D. when the device is removed from the vein or artery, the trapped particles in the filter bag are removed from the treatment site.

11. The device of claim 1, comprising a stylet attached to the distal end of the tubular fabric and being adapted for retraction and release.

12. The method of claim 10, comprising a stylet attached to the distal end of the tubular fabric and being adapted for retraction and release.

* * * * *